United States Patent
Lin

(10) Patent No.: US 6,169,210 B1
(45) Date of Patent: *Jan. 2, 2001

(54) METHOD FOR PRODUCING DIALKYL DISULFIDES

(76) Inventor: Kaung-Far Lin, 430 Woodruff Dr., Baton Rouge, LA (US) 70808

( * ) Notice: Under 35 U.S.C. 154(b), the term of this patent shall be extended for 0 days.

This patent is subject to a terminal disclaimer.

(21) Appl. No.: 09/295,620

(22) Filed: Apr. 20, 1999

(51) Int. Cl.$^7$ .................. C07C 321/14; C07C 319/14

(52) U.S. Cl. .................................. 568/26; 568/21

(58) Field of Search .................. 568/21, 26, 61

(56) References Cited

U.S. PATENT DOCUMENTS

| | | | | |
|---|---|---|---|---|
| 2,001,715 | * | 5/1935 | Fischer | 568/26 |
| 2,517,934 | * | 8/1950 | Schulze | 568/26 |
| 2,558,221 | * | 6/1951 | Mertz | 568/26 |
| 2,574,884 | * | 11/1951 | Mertz | 568/26 |
| 3,143,574 | * | 8/1964 | Brown | 568/26 |
| 3,294,760 | * | 12/1966 | Hay | 528/374 |
| 3,314,999 | | 4/1967 | Bapseres et al. | 260/608 |
| 3,755,461 | | 8/1973 | Kvasnikoff et al. | 260/608 |
| 4,277,623 | | 7/1981 | Kubicek | 568/26 |
| 4,482,744 | * | 11/1984 | Audeh | 568/60 |
| 4,868,336 | * | 9/1989 | Presnall | 568/25 |
| 5,026,915 | | 6/1991 | Buchholz et al. | 568/26 |
| 5,202,494 | | 4/1993 | Roberts et al. | 568/26 |
| 5,312,993 | | 5/1994 | Arretz | 568/26 |
| 5,493,058 | | 2/1996 | Cadot et al. | 568/70 |
| 5,733,836 | | 3/1998 | Stinn et al. | 502/255 |

OTHER PUBLICATIONS

Ross, Robert A., et al., "Catalytic Oxidation of Methyl Mercaptan over Cobalt Molybdate", Ind. Eng. Chem., Prod. Res. Dev., vol. 16, No. 2, 1977, pp. 147–150.

Heyes, Christoper J., et al., "The Catalytic Oxidation of Organic Air Pollutants Part 2. Cobalt Molybdate and Copper Chromite Catalysts", J. Chem. Tech. Biotechnol., 1982, vol. 32, pp. 1034–1041.

Heyes, Christoper J., et al., "The Catalytic Oxidation of Organic Air Pollutants Part 3. Catalysts from Manganese and Copper Sulphates", J. Chem. Tech. Biotechnol., 1985, vol. 35A, pp.89–96.

Schulze, W.A., et al., "Sulfur Compounds from Petroleum Hydrocarbons", Industrial and Engineering Chemistry, vol. 42, No. 5, Mar. 1950, pp. 916–921.

Wiezevich, P.J., et al., "Sulfur Compounds Derived from Petroleum", Reactions & Derivatives of Tertiary Aliphatic Mercaptans, Industrial and Engineering Chemistry, vol. 25, No. 3, May 1933, pp. 295–296.

Wang, Ching–Huei, et al., "Al2O3–Supported Mixed–Metal Oxides for Destructive Oxidation of (CH3)2S2", Ind. Eng. Chem. Res., vol. 36, 1997, pp. 2537–2542.

Heyes, C.J., et al., "The Catalytic Oxidation of Organic Air Pollutants. Part 1. Single Metal Oxide Catalysts", J. Chem. Tech. Biotechnol., 1982, vol. 32, pp. 1025–1033.

Liu, K.T., et al., "A Facile Conversion of Thiols to Disulfides", Communications, Synthesis, Sep. 1978, pp. 669–670.

Stull, D.R. et al., "The Chemical Thermodynamics of Organic Compounds", 1987, Robert E. Krieger Publishing Company, Malabar, Florida, pp. 137, 139, 219, 229, 230, 245, 422, 563, 611.

* cited by examiner

Primary Examiner—Jean F Vollano
(74) Attorney, Agent, or Firm—Philip M. Pippenger

(57) ABSTRACT

A highly efficient method of producing dialkyl disulfides from mercaptans and oxygen is described which involves employing carbon dioxide as an internal coolant. Among the benefits made possible by this method are (1) an increase in the proportion of mercaptan converted to dialkyl disulfide per pass through the reactor, (2) an increased ease of separation of and recycling of carbon dioxide, (3) the ability to use a common contaminant as a coolant, and (4) the use of a simple adiabatic reactor design.

27 Claims, 1 Drawing Sheet

METHOD FOR PRODUCING DIALKYL DISULFIDES

TECHNICAL FIELD

This invention pertains to a novel and highly efficient method for the production of dialkyl disulfides.

BACKGROUND

Dialkyl disulfides are useful as intermediates in the production of various end products. For example, dimethylthiotoluenediamine (DMTDA), a compound used extensively in many injection molding processes, can be produced in a relatively cost efficient manner using dimethyl disulfide prepared pursuant to this invention.

The production of dialkyl disulfides by the metal catalyzed oxidation of mercaptans in the presence of elemental oxygen is not new to the chemical industry. However, the presently utilized processes are still deficient in important areas.

In particular, the large quantities of heat released in the reaction combined with the high efficiency of modem catalysts place an extreme burden on the cooling method employed. A present method of cooling the oxidation reaction involves continuously feeding alkyl mercaptan into the reaction zone in great excess relative to oxygen, with the expectation that unoxidized alkyl mercaptan will function to absorb the heat of reaction generated by the oxidized mercaptan. The above method suffers from a deficiency in that the limiting reagent is oxygen. In order to keep the reaction zone temperature within a specified range, it is necessary that only a fraction of the mercaptan introduced into the reaction zone be converted to dialkyl disulfide; the unoxidized alkyl mercaptan molecules function as a coolant and pass from the reaction zone. As a result, the mercaptan to dialkyl disulfide conversion efficiency after a single pass through the reaction zone is significantly less than one, and corrosive mercaptan must be continuously recycled and rehandled.

Another problem with the presently practiced methods of producing dialkyl disulfides from mercaptans is that a convenient carbon dioxide recycle process for producing mercaptans from hydrogen sulfide and methanol yields a product containing extremely high amounts of carbon dioxide. In order to obtain pure mercaptan to feed into the reaction zone, it is necessary to separate the carbon dioxide from the mercaptan.

Another problem with currently practiced methods for converting alkyl mercaptans to dialkyl disulfides is that the reactor is typically not a simple adiabatic reactor. Due to the fact that external coolant is generally necessary, the reactor is of a relatively expensive and complicated nonadiabatic design.

It would represent a significant advance in the state of the art if a method could be discovered which (1) improves the one-pass conversion efficiency of the oxidation reaction, thus eliminating the recycling and rehandling of the corrosive mercaptan, (2) allows direct utilization of the carbon dioxide recycle process product, thus eliminating the separation of mercaptan and carbon dioxide, and (3) enables the use of a simple and inexpensive adiabatic reactor design.

SUMMARY OF THE INVENTION

Pursuant to this invention, carbon dioxide is used as a coolant in the place of the mercaptan component used heretofore in the reaction of alkyl mercaptan and oxygen to give dialkyl disulfide. By so doing, the alkyl mercaptan conversion efficiency after one pass through the reaction zone can be raised to nearly one hundred percent. Moreover, carbon dioxide can be readily and easily separated from the dialkyl disulfide product, and this in turn greatly facilitates the removal of and recycling of the coolant. In addition, mercaptan which is contaminated with high amounts of carbon dioxide, a mixture which is available from other industrial processes, can be fed into the reaction zone without first separating out the carbon dioxide. Thus, this invention provides a convenient and highly efficient process for making dialkyl disulfides from alcohols, hydrogen sulfide, and oxygen. Additionally, since carbon dioxide functions as an internal coolant, a simple adiabatic reactor design can be used.

Accordingly, one embodiment of this invention is a process for producing dialkyl disulfides, which process comprises:

A) continuously introducing into a reaction zone components comprising (i) a mercaptan, (ii) elemental oxygen, and (iii) carbon dioxide to form a reaction mixture and contacting said mixture in said reaction zone with a solid phase catalyst such that a product mixture comprising dialkyl disulfide and carbon dioxide is formed; and B) continuously withdrawing product mixture from said reaction zone.

As noted above, this invention enables the use of carbon dioxide contaminated feedstreams. In fact, the carbon dioxide contaminant can be present in either or both reactant feedstreams.

After functioning as a coolant in the reaction, it is preferable to separate the carbon dioxide from the dialkyl disulfide product, cool the carbon dioxide, and reintroduce it into the reactor with incoming reactants to give continued cooling benefits.

The repeated removal and recycling of carbon dioxide results in the accumulation of a substantial recycled stream during continuous operation. Likewise, a source of "fresh" carbon dioxide can be used instead of or in addition to a recycled stream of carbon dioxide. Thus, it can be desirable to begin the process with fresh carbon dioxide as the coolant, and decrease its usage as a recycle stream is generated. If a reactant source contains carbon dioxide, dependence upon fresh carbon dioxide can be reduced more quickly.

Thus in another embodiment, this invention provides for a process for producing dialkyl disulfides, which process comprises:

A) continuously introducing into a reaction zone components comprising (i) a mercaptan, (ii) elemental oxygen, and (iii) carbon dioxide to form a reaction mixture and contacting said mixture in said reaction zone with a solid phase catalyst such that a product mixture comprising dialkyl disulfide and carbon dioxide is formed;

B) continuously withdrawing product mixture from said reaction zone;

C) separating from said mixture all or a portion of the carbon dioxide present therein; and D) recycling all or a portion of the carbon dioxide from C) to A).

An additional aspect of the process of this invention is that it enables the efficient linking of the dialkyl disulfide formation reaction with the mercaptan formation reaction. Such integration is especially convenient when the mercaptan source is contaminated with carbon dioxide.

In commonly owned co-pending Ser. No. 09/295,622, filed Apr. 20, 1999, an efficient process for producing alkyl mercaptans in which carbon dioxide is used as an internal coolant is disclosed, which process comprises: A) continuously introducing into a reaction zone components comprising (i) an alkanol, (ii) hydrogen sulfide, and (iii) carbon dioxide to form a vapor phase reaction mixture and contacting said mixture in said reaction zone with a solid phase catalyst such that a vapor phase product mixture comprising alkyl mercaptan and/or dialkyl monosulfide is formed; and B) continuously withdrawing from said reaction zone a mixture comprising alkyl mercaptans and carbon dioxide.

If the alkyl mercaptan is formed in a process which utilizes the addition of carbon dioxide as a coolant, it is preferable to recycle all or a portion of the carbon dioxide separated from the dialkyl disulfide product back into the mercaptan formation reaction. On the other hand, if it is the case that the mercaptan is formed in a process in which the carbon dioxide has other origins, e.g., a contaminated reactant stream, it can be preferable to recycle all or a portion of the carbon dioxide separated from the dialkyl disulfide product back into the dialkyl disulfide formation reaction. Both types of recycle can be used if it is deemed advantageous to do so.

If desired, the mercaptan/carbon dioxide mixture resulting from the mercaptan formation reaction can be cooled before introduction of said mixture into the dialkyl disulfide formation reaction zone in order to control the temperature in the zone. Additionally or alternatively, the temperature in the dialkyl disulfide reaction zone can be controlled by cooling the carbon dioxide which has been separated from the dialkyl disulfide product before reintroducing said carbon dioxide into the dialkyl disulfide formation zone.

The separation of carbon dioxide from a dialkyl disulfide is generally much more easily accomplished than the separation of carbon dioxide from the corresponding mercaptan, alkyl alcohol or hydrogen sulfide. It is thus preferable to form mercaptan from alkanol and hydrogen sulfide, with carbon dioxide as a contaminant or coolant, convert the mercaptan in the product mixture to dialkyl disulfide by the process of the invention, and separate the carbon dioxide from the dialkyl disulfide. In this manner, dialkyl disulfides can be prepared from alkanols, hydrogen sulfide, and oxygen; what would otherwise have been a contaminant is used as a coolant in the dialkyl disulfide reaction; and the removal of carbon dioxide can be greatly simplified, facilitating continued recycling.

Thus, an additional embodiment of the invention is a process for producing dialkyl disulfides, which process comprises:

A) continuously introducing into a reaction zone components comprising (i) an alcohol, (ii) hydrogen sulfide, and (iii) carbon dioxide to form a vapor phase reaction mixture, and contacting said mixture with a solid phase catalyst such that a vapor phase product mixture comprising mercaptan and carbon dioxide is formed;

B) continuously withdrawing said vapor phase product mixture from said reaction zone;

C) separating from said mixture all or a portion of the carbon dioxide present therein;

D) recycling all or a portion of the carbon dioxide from C) to A);

E) continuously introducing into a reaction zone components comprising (a) mercaptan formed in A), (b) elemental oxygen, and (c) carbon dioxide to form a reaction mixture, and contacting said reaction mixture with a solid phase catalyst such that a product mixture comprising dialkyl disulfide and carbon dioxide is formed;

F) continuously withdrawing said product mixture from said reaction zone;

G) separating all or a portion of the carbon dioxide from the withdrawn product mixture of F); and H) recycling all or a portion of the carbon dioxide from G) to E) and/or A).

In the above embodiments, highly sensitive temperature control can be realized by the adjustment of input of recycled and/or fresh carbon dioxide into the reaction zone. Typically, temperature control is effected by altering the molar ratios of carbon dioxide to reactants introduced into the reaction zone.

The above and other embodiments will be apparent from the ensuing description and appended claims.

The following is an illustration of the feasibility of dialkyl disulfide production with carbon dioxide as a recycled coolant. It is not intended to constitute a limit on the invention, but is presented for purposes of illustration.

FURTHER DETAILED DESCRIPTION

Figure 1:
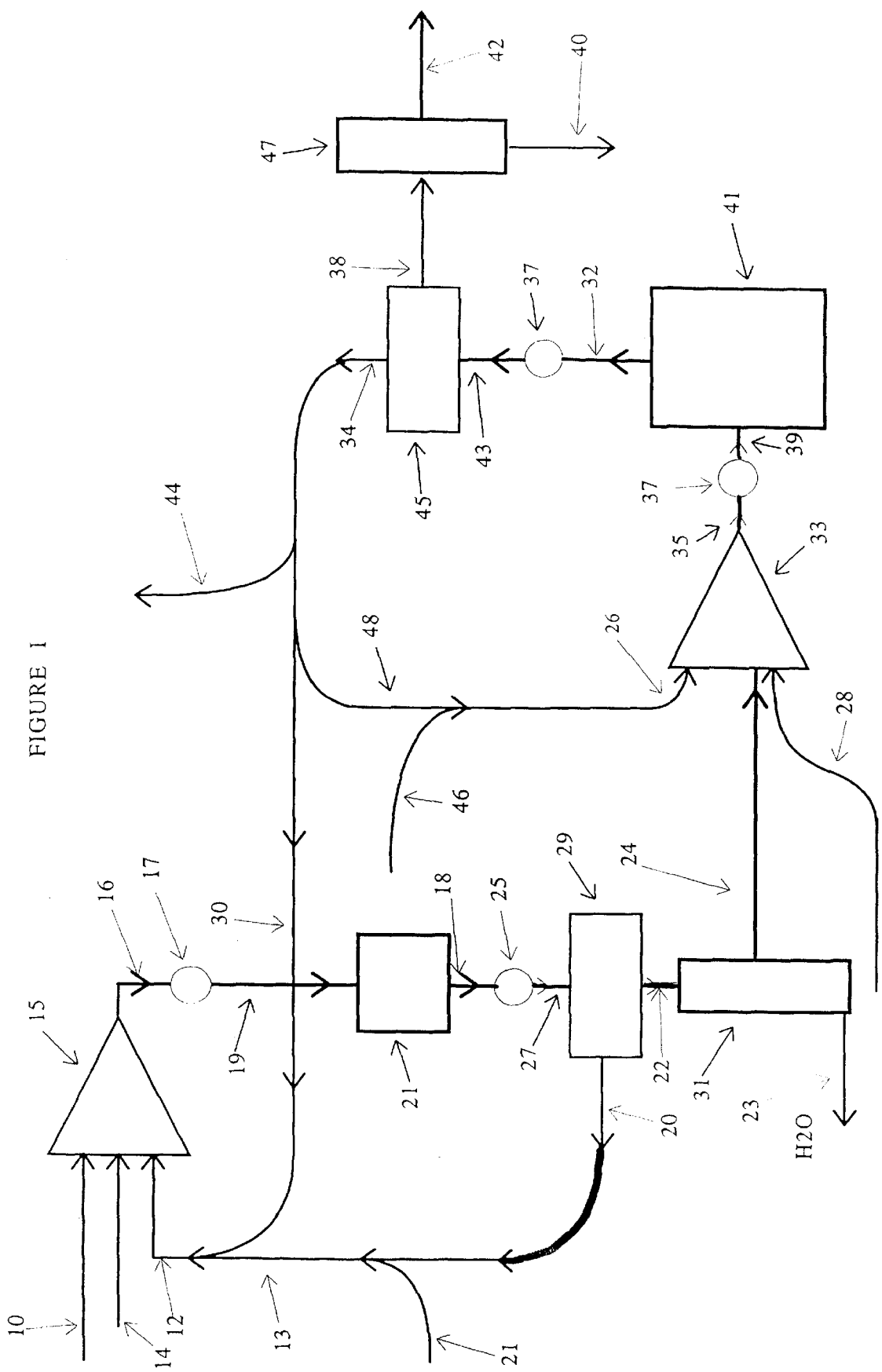
FIG. 1 is a schematic flowsheet illustrating a method of producing dimethyl disulfide pursuant to this invention in an embodiment wherein recycle of carbon dioxide is employed.

The mercaptans utilized in the practice of this invention typically contain less than about 12 carbon atoms. Primary, secondary, tertiary or aromatic mercaptans can be used in the process of this invention. Suitable mercaptans include: methyl mercaptan, ethyl mercaptan, propyl mercaptan, isopropyl mercaptan, 1-butyl mercaptan, 2-butyl mercaptan, isobutyl mercaptan, tert-butyl mercaptan, pentyl mercaptan, 2-pentyl mercaptan, 3-pentyl mercaptan, 2-heptyl mercaptan, 3-nonyl mercaptan, 4-decyl mercaptan, cyclopentyl mertan, cyclohexyl mercaptan, benzyl mercaptan, and similar compounds. Preferably, a mercaptan of less than about 10 carbon atoms is used. Most preferably, methyl mercaptan is used.

Typically, the mercaptan is introduced into the reactor with oxygen in amounts such that the mole ratio of mercaptan to oxygen is in the range of about 1 mole of mercaptan per mole of oxygen to about 4 moles of mercaptan per mole of oxygen. Preferably, the mole ratio is in the range of about 2 moles of mercaptan per mole of oxygen to about 4 moles of mercaptan per mole of oxygen. Most preferably, the mole ratio is in the range of about 3.5 moles of mercaptan per mole of oxygen to about 3.7 moles of mercaptan per mole of oxygen.

Carbon dioxide may be introduced into the reaction zone in the same stream as one or both of the ants, and/or it may be introduced in a stream separate from either reactant. It is preferable that the mole ratio of (1) the carbon dioxide introduced into the reaction zone, to (2) the total amount of elemental oxygen introduced into the reaction zone be in the range of about 10 moles of carbon dioxide per mole of oxygen to about 500 moles of carbon dioxide per mole of oxygen. A mole ratio in the range of about 20 moles of carbon dioxide per mole of oxygen to about 100 moles of carbon dioxide per mole of oxygen is more preferable. Most preferable is a ratio in the range of about 35 moles of carbon dioxide per mole of oxygen to about 45 moles of carbon dioxide per mole of oxygen.

The catalyst is typically comprised of a refractory support in which, optionally, one or more metals may be impregnated. Suitable materials for a refractory support include, but are not limited to materials such as alumina, silica, alumina-silica, chromia, and the like. γ-Alumina is particularly suitable. Such a support is usually doped with the oxide of one or more metals, often an alkaline earth metal oxide alone or in combination with an alkali metal oxide. Other oxides such as transition metal oxides can be used as well. Group I and Group II elements such as sodium, potassium, magnesium and strontium, as well as transition metals such as copper, molybdenum, chromium, iron, tungsten, manganese, nickel, zinc, molybdenum, cobalt and lanthanum can be used. Preferred dopants are the oxides of sodium, magnesium, copper, iron, tungsten, nickel, molybdenum and cobalt. Most preferred are oxides of copper and sodium.

If a γ-alumina catalyst which is doped with copper oxide and sodium oxide is used in the process of this invention, it is desirable to have a weight ratio of copper oxide to γ-alumina in the range of about 0.02 gram of copper oxide per gram of γ-alumina to about 0.2 gram of copper oxide per gram of γ-alumina. Most desirable is a weight ratio of copper oxide to γ-alumina in the range of about 0.08 gram of copper oxide per gram of γ-alumina to about 0.12 gram copper oxide per gram of γ-alumina. In addition, it is preferable to have a weight ratio of sodium oxide to γ-alumina in the range of about 0.01 gram of sodium oxide per gram of γ-alumina to 0.1 gram of sodium oxide per gram of γ-alumina. Most preferred is a weight ratio of sodium oxide to γ-alumina in the range of about 0.04 gram of sodium oxide per gram of γ-alumina to about 0.06 gram of sodium oxide per gram of γ-alumina.

Appropriate catalysts can be prepared using methods well known in the art. One such method involves dipping the chosen refractory support in an aqueous solution of the carbonate, acetate, nitrate, hydroxide, or other suitable salt of the appropriate metal. After drying, the catalyst is then calcined. More information with respect to catalyst preparation can be found in U.S. Pat. No. 5,733,836.

Catalysts based on non-metals can also be used. One type of suitable catalysts is the group composed of basic macroreticular polystyrene-divinyl benzene copolymers. An example of such is "AMBERLYST" by Rohm and Haas. In addition, zeolites, as well as clays which are impregnated with a metal salt such as copper chloride can be utilized.

It is desirable for the catalyst to occupy at least 50% of the reaction zone. It is most desirable for the catalyst to occupy at least 70% of the reaction zone. The volume occupied by the catalyst as referred to here is meant to include the spaces inside the catalyst pores as well as the spaces between the catalyst particles. Thus, for example, the catalyst occupies approximately 70% of the volume of a 100 mL graduated cylinder if the cylinder is filled to the 70 ml mark with catalyst particles, even though the actual space occupied by the catalyst may be significantly less. The reaction zone and the catalyst can be used together as a fixed bed or as a fluidized bed.

Preferably, the catalyst has a surface area in the range of about 100 square meters per gram to about 300 square meters per gram. More preferably, the catalyst has a surface area in the range of about 150 to about 250 square meters per gram. Most preferably, the catalyst has a surface area of about 200 square meters per gram.

It is desirable for the reaction mixture to have a vapor space time in the reaction zone in the range of about 0.002 second to about 20 seconds. It is more desirable for the reaction mixture to have a vapor space time to be in the range of about 0.02 to about 2 seconds. Most desirable is a vapor space time in the range of about 0.1 to about 0.3 second. The vapor space time is defined to be the reaction zone volume divided by the reaction mixture volumetric flow rate.

The process of this invention can be conducted at a wide range of temperatures. It is most preferable to have a temperature in the reaction zone in the range of about 20° C. to about 400° C. Most preferable is a temperature in the range of about 100° C. to about 200° C.

It is preferred that the pressure in the reaction zone be in the range of about 50 psia to about 500 psia. Most preferred is a pressure in the range of about 90 psia to about 110 psia.

FIG. 1 illustrates process flows that can be employed in a plant producing dialkyl disulfide pursuant to this invention. In the operation depicted, carbon dioxide is employed as a recycled coolant. It will be understood and appreciated that the process depicted in FIG. 1 and as described below is not intended to limit, and should not be construed as limiting, the scope of this invention.

In the embodiment depicted in FIG. 1, methanol and a mixture of hydrogen sulfide and carbon dioxide are fed via lines 10 and 12, respectively into static mixer 15. Additional carbon dioxide from a separate source can be fed to mixer 15, as needed, via line 14 to maintain the desired feed proportions of methanol, carbon dioxide and hydrogen sulfide. The hydrogen sulfide/carbon dioxide feed in line 12 is composed of carbon dioxide emanating from lines 20, 21 and 30. The carbon dioxide in lines 20 and 30 is derived from recycle operations specified below. The carbon dioxide/hydrogen sulfide mixture in line 21 is derived from an ancillary operation. In embodiments where such ancillary feed of hydrogen sulfide/carbon dioxide is not employed, hydrogen sulfide can be fed via line 21. The rates at which these feeds are maintained are such that the molar ratio of methanol to hydrogen sulfide in the mixture is about 1 mole of methanol per mole of hydrogen sulfide, and the molar ratio of hydrogen sulfide to carbon dioxide in the mixture is about 0.5 mole of methanol per mole of carbon dioxide.

The effluent of static mixer 15 is fed via line 16 into heater 17, where it is heated to 300° C. The heated mixture is then fed via line 19 into methyl mercaptan reactor 21. Reactor 21 has a diameter of 0.5 inch and a length of 17 inches. The γ-alumina catalyst in reactor 21 has a surface area of about 200 square meters per gram. It is doped with about 4 wt % $K_2O$ and about 9 wt % $W_2O_3$. The catalyst occupies roughly 90% of the reactor, excluding the space between the catalyst granules, as well as in the pores of the granules. The vapor space time of the mixture in the reactor is about 60 seconds.

The effluent from the methyl mercaptan reactor is fed via line 18 into cooler 25, where it is cooled to about 60° C. The cooled mixture is then fed via line 27 into flash unit 29 where the much of the carbon dioxide is separated from the mixture, leaving flash unit 29 via line 20. The remainder of the reaction mixture exits flash unit 29 via line 22, and enters decanter 31, where water is separated from the mixture. The separated water leaves the decanter via line 23, and the remainder of the reaction mixture, comprised of methyl mercaptan and carbon dioxide, leaves the decanter via line 24.

The methyl mercaptan/carbon dioxide mixture, air (oxygen), and carbon dioxide are fed into static mixer 33 via lines 24, 28 and 26, respectively. The effluent of static mixer 33 is fed via line 35 into heater 37, where it is heated to 100°

C. The heated mixture is then fed via line 39 into DMDS reactor 41, which has a diameter of 0.5 inch and a length of 17 inches. The catalyst in reactor 41 is γ-alumina doped with roughly 10 wt % CuO and about 5 wt % $Na_2O$. It has a surface area of roughly 200 square meters per gram. The vapor space time in the reactor is about 0.2 second. The catalyst occupies roughly 90% of the reactor excluding the space between and in the pores of the catalyst granules. The effluent from DMDS reactor 41 is then fed via line 32 into cooler 37, where it is cooled to 100° C. The cooled mixture is then fed via line 43 into flash unit 45, where carbon dioxide is separated from the reaction mixture. The separated carbon dioxide leaves flash unit 45 via line 34. The remainder of the reaction mixture leaves flash unit 45 via line 38, and is fed into decanter 47, where water is removed. The water leaves the decanter via line 40, and the DMDS leaves decanter 47 via line 42. In the depicted embodiment, after carbon dioxide leaves flash 45 via line 34, it splits into three branches: lines 30, 44 and 48. An optional ancillary source of carbon dioxide is combined with line 48 via line 46 to form line 26. Line 30 is combined with line 13 to give line 12, and line 44 is a purge. Line 34 is proportioned between lines 30, 44 and 48 such that the molar ratio of methyl mercaptan to oxygen entering static mixer 33 is about 3.6 moles of methyl mercaptan per mole of oxygen, and the mole ratio of carbon dioxide to oxygen is about 40 moles of carbon dioxide per mole of oxygen.

It is to be understood that the reactants and components referred to by chemical name or by formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient just as it existed at the time just before it was first contacted, blended or mixed with one or more other substances, components and/or ingredients in accordance with the present disclosure. Thus the fact that a substance, component or ingredient may have lost its original identity through a chemical reaction or transformation through the course of contacting, blending or mixing operations, if conducted in accordance with this disclosure and with the application of common sense and the ordinary skill of a chemist, is wholly immaterial for an accurate understanding and appreciation of the true meaning and substance of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for producing dialkyl disulfides, which process comprises:

A) continuously introducing components comprising (I) a mercaptan, (II) elemental oxygen, and (III) carbon dioxide into contact with a solid phase catalyst in a reaction zone such that dialkyl disulfide is formed in said reaction zone; and B) continuously withdrawing from said reaction zone, a mixture comprising dialkyl disulfide and carbon dioxide.

2. A process as in claim 1 wherein the mole ratio of (I) to (II) introduced into the reaction zone is in the range of about 1 to about 4 moles of (I) per mole of (II).

3. A process as in claim 1 wherein the mole ratio of (III) to (II) introduced into the reaction zone is in the range of about 10 to about 500 moles of (II) per mole of (II).

4. A process as in claim 1 wherein the temperature in the reaction zone is in the range of about 20° C. to about 400° C.

5. A process as in claim 1 wherein the catalyst is a composition comprised of (a) aluminum oxide, and (b) a transition metal oxide and/or one or more alkali metal or alkaline earth metal oxides.

6. A process as in claim 1 wherein the pressure in the reaction zone is in the range of about 50 psia to about 500 psia.

7. A process as in claim 1 wherein (I) is methyl mercaptan.

8. A process as in claim 1 wherein (I) is methyl mercaptan, wherein the mole ratio of (I) to (II) introduced into the reaction zone is in the range of about 1 to about 4 moles of (I) per mole of (II), wherein the mole ratio of (III) to (II) introduced into the reaction zone is in the range of about 10 to about 500 moles of (III) per mole of (II), and wherein the temperature in the reaction zone is in the range of about 20° C. to about 400° C.

9. A process as in claim 1 wherein the vapor space time is in the range of about 0.002 second to about 20 seconds, and wherein the catalyst has a surface area in the range of about 100 square meters per gram to about 300 square meters per gram.

10. A process as in claim 1 wherein the catalyst is a composition comprised of (a) γ-aluminum oxide, (b) copper oxide, and (c) sodium oxide, wherein the weight ratio of (b) to (a) is in the range of about 0.02 to about 0.20 gram of (b) per gram of (a), wherein the weight ratio of (c) to (a) is in the range of about 0.01 to about 0.10 gram of (c) per gram of (a).

11. A process as in claim 10 wherein (I) is methyl mercaptan.

12. A process as in claim 1 wherein (I) is methyl mercaptan, wherein the mole ratio of (I) to (II) introduced into the reaction zone is in the range of about 3.5 moles of (I) per mole of (II) to about 3.7 moles of (I) per mole of (II), wherein the mole ratio of (III) to (II) introduced into the reaction zone is in the range of about 35 moles of (III) per mole of (II) to about 45 moles of (III) per mole of (II), wherein the temperature in the reaction zone is in the range of about 100° C. to about 200° C., wherein the pressure in the reaction zone is in the range of about 90 psia to about 110 psia, wherein the catalyst is a composition comprised of (a) γ-alumina, (b) copper oxide, and (c) sodium oxide, wherein the weight ratio of (b) to (a) is in the range of about 0.08 gram of (b) per gram of (a) to about 0.12 gram of (b) per gram of (a), wherein the weight ratio of (c) to (a) is in the range of about 0.04 gram of (c) per gram of (a) to about 0.06 gram of (c) per gram of (a), wherein the vapor space time is in the range of about 0.1 second to about 0.3 second, and the catalyst has a surface area of about 200 square meters per gram.

13. A process as in claim 1 wherein all or a portion of the carbon dioxide present in the mixture withdrawn from the reaction zone is separated from the mixture, and subsequently utilized in another process carried out according to claim 1.

14. A process as in claim 12 wherein all or a portion of the carbon dioxide present in the mixture withdrawn from the reaction zone is separated from the mixture, and subsequently utilized in another process carried out according to claim 12.

15. A process as in claim 1 or 13 wherein (I) is formed by a process which comprises:
   A) continuously introducing into a reaction zone components comprising (i) an alcohol, (ii) hydrogen sulfide, and (iii) carbon dioxide to form a vapor phase mixture thereof and contacting said mixture with a solid phase catalyst such that a vapor phase mixture comprising alkyl mercaptan is formed in said reaction zone;
   B) continuously withdrawing from said reaction zone, a vapor phase mixture comprising alkyl mercaptan and carbon dioxide;
   C) separating from the mixture withdrawn in B), all or a portion of the carbon dioxide present therein; and
   D) recycling carbon dioxide from C) to A).

16. A process as in claim 12 or 14 wherein (I) is formed by a process which comprises:
   A) continuously introducing into a reaction zone components comprising (i) methanol, (ii) hydrogen sulfide, and (iii) carbon dioxide to form a vapor phase mixture thereof and contacting said mixture with a solid phase catalyst such that a vapor phase mixture comprising methyl mercaptan is formed in said reaction zone;
   B) continuously withdrawing from said reaction zone, a vapor phase mixture comprising methyl mercaptan and carbon dioxide;
   C) separating from the mixture withdrawn in B), all or a portion of the carbon dioxide present therein; and
   D) recycling carbon dioxide from C) to A).

17. A process as in claim 1 or 13, wherein (I) is formed by a process which comprises:
   A) continuously introducing into a reaction zone components comprising (i) an alcohol, (ii) hydrogen sulfide, and (iii) carbon dioxide to form a vapor phase mixture thereof, and contacting said mixture with a solid phase catalyst such that a vapor phase mixture comprising alkyl mercaptan is formed in said reaction zone;
   B) continuously withdrawing from said reaction zone, a vapor phase mixture comprising alkyl mercaptan and carbon dioxide;
   C) separating from the mixture withdrawn in B), all or a portion of the carbon dioxide present therein; and
   D) recycling all or a portion of the carbon dioxide from C) to A);
wherein the mole ratio of (i) to (ii) introduced into the reaction zone is in the range of about 0.9 mole of (i) per mole of (ii) to about 1.1 moles of (i) per mole of (ii), wherein the mole ratio of (ii) to (iii) introduced into the reaction zone is in the range of about 0.4 mole of (ii) per mole of (iii) to about 0.6 mole of (ii) per mole of (iii), wherein the temperature in the reaction zone is in the range of about 360° C. to about 380° C., wherein the pressure in the reaction zone is in the range of about 110 psia to about 130 psia, wherein the catalyst is a composition comprised of (1) γ-alumina, (2) potassium oxide, (3) tungsten oxide, wherein the weight ratio of (2) to (1) is in the range of about 0.035 gram of (2) per gram of (1) to about 0.045 gram of (2) per gram of (1), wherein the weight ratio of (3) to (1) is in the range of about 0.085 gram of (3) per gram of (1) to about 0.095 gram of (3) per gram of (1), wherein the vapor space time is in the range of about 8 seconds to about 12 seconds, and wherein the catalyst has a surface area of about 200 square meters per gram.

18. A process as in claim 12 or 14, wherein (I) is formed by a process which comprises:
   A) continuously introducing into a reaction zone components comprising (i) methanol (ii) hydrogen sulfide, and (iii) carbon dioxide to form a vapor phase mixture thereof and contacting said mixture with a solid phase catalyst such that a vapor phase mixture comprising methyl mercaptan is formed in said reaction zone;
   B) continuously withdrawing from said reaction zone, a vapor phase mixture comprising methyl mercaptan and carbon dioxide;
   C) separating from the mixture withdrawn in B), all or a portion of carbon dioxide present therein; and
   D) recycling all or a portion of the carbon dioxide from C) to A);
wherein the mole ratio of (i) to (ii) introduced into the reaction zone is in the range of about 0.9 mole of (i) per mole of (ii) to about 1.1 moles of (i) per mole of (ii), wherein the mole ratio of (ii) to (iii) introduced into the reaction zone is in the range of about 0.4 mole of (ii) per mole of (iii) to about 0.6 mole of (ii) per mole of (iii), wherein the temperature in the reaction zone is in the range of about 360° C. to about 380° C., wherein the pressure in the reaction zone is in the range of about 110 psia to about 130 psia, wherein the catalyst is a composition comprised of (1) γ-alumina, (2) potassium oxide, (3) tungsten oxide, wherein the weight ratio of (2) to (1) is in the range of about 0.035 gram of (2) per gram of (1) to about 0.045 gram of (2) per gram of (1), wherein the weight ratio of (3) to (1) is in the range of about 0.085 gram of (3) per gram of (1) to about 0.095 gram of (3) per gram of (1), wherein the vapor space time is in the range of about 8 seconds to about 12 seconds, and wherein the catalyst has a surface area of about 200 square meters per gram.

19. A process for producing dialkyl disulfides, which process comprises:
   A) continuously introducing into a first reaction zone components comprising (i) an alcohol, (ii) hydrogen sulfide, and (iii) carbon dioxide so that a vapor phase mixture is formed, and contacting said mixture with a solid phase catalyst such that a vapor phase mixture comprising alkyl mercaptan is formed in said reaction zone;
   B) continuously withdrawing from said first reaction zone, a vapor phase mixture comprising alkyl mercaptan and carbon dioxide;
   C) separating from the mixture withdrawn in B), all or a portion of the carbon dioxide present therein;
   D) recycling all or a portion of the separated carbon dioxide from C) to A);
   E) continuously introducing into a second reaction zone components comprising (I) alkyl mercaptan formed in A), (II) elemental oxygen, and (III) carbon dioxide so that a second mixture is formed and contacting said second mixture with a solid phase catalyst such that a product-containing mixture comprising dialkyl disulfide is formed in said reaction zone;
   F) continuously withdrawing said product-containing mixture from said second reaction zone;

G) separating from the withdrawn product mixture of F), all or a portion of the carbon dioxide present therein; and H) recycling all or a portion of the separated carbon dioxide from G) to E) and/or A).

20. A process as in claim 19 wherein (i) is methanol and (I) is methyl mercaptan, wherein the mole ratio of (I) to (II) introduced into the reaction zone of E) is in the range of about 3.5 moles of (I) per mole of (II) to about 3.7 moles of (I) per mole of (II), wherein the mole ratio of (III) to (II) introduced into the reaction zone of E) is in the range of about 35 moles of (III) per mole of (II) to about 45 moles of (III) per mole of (II), wherein the temperature of the reaction zone in E) is in the range of about 100° C. to about 200° C., wherein the pressure in the reaction zone in E) is in the range of about 90 psia to about 110 psia, wherein the catalyst in E) is a composition comprised of (a) γ-alumina, (b) copper oxide, (c) sodium oxide, wherein the weight ratio of (b) to (a) is in the range of about 0.08 gram of (b) per gram of (a) to about 0.12 gram of (b) per gram of (a), wherein the weight ratio of (c) to (a) is in the range of about 0.04 gram of (c) per gram of (a) to about 0.06 gram of (c) per gram of (a), wherein the vapor space time is in the range of about 0.1 second to about 0.3 second, and wherein the catalyst has a surface area of about 200 square meters per gram.

21. A process as in claim 19 wherein (i) is methanol, wherein the mole ratio of (i) to (ii) introduced into the reaction zone of A) is in the range of about 0.9 mole of (i) per mole of (ii) to about 1.1 moles of (i) per mole of (ii), wherein the mole ratio of (ii) to (iii) introduced into the reaction zone of A) is in the range of about 0.4 mole of (ii) per mole of (iii) to about 0.6 mole of (ii) per mole of (iii), wherein the temperature of the reaction zone of A) is in the range of about 360° C. to about 380° C., wherein the pressure in the reaction zone of A) is in the range of about 110 psia to about 130 psia, wherein the catalyst in A) is a composition comprised of (1) γ-alumina, (2) potassium oxide, and (3) tungsten oxide, wherein the weight ratio of (2) to (1) is in the range of about 0.035 gram of (2) per gram of (1) to about 0.045 gram of (2) per gram of (1), wherein the weight ratio of (3) to (1) is in the range of about 0.085 gram of (3) per gram of (1) to about 0.095 gram of (3) per gram of (1), wherein the vapor space time is in the range of about 8 seconds to about 12 seconds, and wherein the catalyst has a surface area of about 200 square meters per gram.

22. A process for producing dialkyl disulfides, which process comprises:

A) continuously introducing components comprising (i) an alcohol, (ii) hydrogen sulfide, and (iii) carbon dioxide into contact with a solid phase catalyst in a first reaction zone such that alkyl mercaptan is formed and is in a vapor phase mixture comprising alkyl mercaptan and carbon dioxide;

B) continuously introducing (I) alkyl mercaptan, at least a portion of which is from said vapor phase mixture in A), (II) elemental oxygen, and (III) carbon dioxide, at least a portion of which is from said vapor phase mixture in A) into contact with a solid phase catalyst in a second reaction zone such that dialkyl disulfide is formed and is in a product-containing vapor phase mixture comprising dialkyl disulfide and carbon dioxide;

C) continuously recovering said product-containing mixture from said second reaction zone.

23. A process as in claim 22 further comprising recovering dialkyl disulfide from the product-containing mixture from C), and recycling to A) at least a portion of the carbon dioxide from the product-containing mixture.

24. A process as in claim 22 or 23 wherein the alcohol is methanol.

25. A process as in claim 22 or 23 wherein:

a) the mole ratio of (i) to (ii) introduced into the first reaction zone is in the range of about 0.9 to about 1.1 moles of (i) per mole of (ii); the mole ratio of (ii) to (iii) introduced into the first reaction zone is in the range of about 0.4 to about 0.6 mole of (ii) per mole of (iii); the temperature in the first reaction zone is in the range of about 360° C. to about 380° C.; and the pressure in the first reaction zone is in the range of about 110 psia to about 130 psia; and b) the mole ratio of (I) to (II) introduced into the second reaction zone is in the range of about 1 to about 4 moles of (I) per mole of (II); the mole ratio of (III) to (II) introduced into the second reaction zone is in the range of about 10 to about 500 moles of (III) per mole of (II); the temperature in the second reaction zone is in the range of about 20° C. to about 400° C.; and the pressure in the second reaction zone is in the range of about 50 psia to about 500 psia.

26. A process as in claim 25 wherein:

c) the catalyst in the first reaction zone is a composition comprised of (1) γ-alumina, (2) potassium oxide, and (3) tungsten oxide, the weight ratio of (2) to (1) is in the range of about 0.035 to about 0.045 gram of (2) per gram of (1), and the weight ratio of (3) to (1) is in the range of about 0.085 to about 0.095 gram of (3) per gram of (1), and d) the catalyst in the second reaction zone is a composition comprised of (a) γ-alumina, (b) copper oxide, and (c) sodium oxide, the weight ratio of (b) to (a) is in the range of about 0.08 to about 0.12 gram of (b) per gram of (a), and the weight ratio of (c) to (a) is in the range of about 0.04 to about 0.06 gram of (c) per gram of (a).

27. A process as in claim 26 wherein the vapor space time in the first reaction zone is in the range of about 8 to about 12 seconds, and wherein the vapor space time in the second reaction zone is in the range of about 0.1 to about 0.3 second.

* * * * *